US011568997B2

(12) United States Patent
Sun et al.

(10) Patent No.: US 11,568,997 B2
(45) Date of Patent: Jan. 31, 2023

(54) DYNAMIC CONTEXT-BASED COLLABORATIVE MEDICAL CONCEPT INTERPRETER

(71) Applicant: International Business Machines Corporation, Armonk, NY (US)

(72) Inventors: Si Sun, Whitestone, NY (US); Pei-Yun Hsueh, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 409 days.

(21) Appl. No.: 16/519,214

(22) Filed: Jul. 23, 2019

(65) Prior Publication Data

US 2021/0027898 A1 Jan. 28, 2021

(51) Int. Cl.
| | | |
|---|---|---|
| *G16H 80/00* | (2018.01) | |
| *G16H 50/20* | (2018.01) | |
| *G16H 10/60* | (2018.01) | |
| *G16H 50/70* | (2018.01) | |
| *G16H 10/40* | (2018.01) | |

(52) U.S. Cl.
CPC .............. *G16H 80/00* (2018.01); *G16H 10/60* (2018.01); *G16H 50/20* (2018.01); *G16H 10/40* (2018.01); *G16H 50/70* (2018.01)

(58) Field of Classification Search
CPC ........ G16H 80/00; G16H 10/60; G16H 50/20; G16H 10/40; G16H 50/70
See application file for complete search history.

(56) References Cited

U.S. PATENT DOCUMENTS 8,147,419 B2   4/2012   Krauss et al.
9,602,559 B1   3/2017   Barros et al.
(Continued)

FOREIGN PATENT DOCUMENTS

CN   102663129 A   9/2012
CN   103177108 A   6/2013
(Continued)

OTHER PUBLICATIONS

"Get The Iodine Medical Translator, Our new Chrome Extension", https://blog.iodine.com/get-the-iodine-medical-translator-our-new-chrome-extension-d15485383823, Downloaded from the internet May 6, 2019, 4 pages.

(Continued)

*Primary Examiner* — Robert A Sorey
*Assistant Examiner* — Kristine K Rapillo
(74) *Attorney, Agent, or Firm* — Stephen J. Walder, Jr.; Kristofer Haggerty

(57) ABSTRACT

A mechanism is provided for implementing a dynamic context-based collaborative medical concept interpreter for automatically generating and presenting summarized explanations of medical concepts. The dynamic context-based collaborative medical concept interpreter performs natural language processing on a real-time patient-provider communication to identify one or more medical concepts referred to in the communication. The dynamic context-based collaborative medical concept interpreter adjusts one or more previous explanations for the one or more medical concepts referred to in the communication using a set of contextual factors. The dynamic context-based collaborative medical concept interpreter generates an abstractive summary that summarizes ranked explanations of the one or more medical concepts based on an original language used in the one or more previous explanations. The dynamic context-based collaborative medical concept interpreter presents, in real time, the abstractive summaries of the one or more medical concepts to the patient and the provider in real-time patient-provider communication.

19 Claims, 5 Drawing Sheets

(56) References Cited

U.S. PATENT DOCUMENTS

| | | |
|---|---|---|
| 2005/0216252 A1 | 9/2005 | Schoenbach et al. |
| 2009/0070103 A1* | 3/2009 | Beggelman ............. G06F 40/20 704/9 |
| 2012/0197876 A1 | 8/2012 | Morris et al. |
| 2013/0132308 A1 | 5/2013 | Boss et al. |
| 2013/0311201 A1* | 11/2013 | Chatfield ............... G16H 15/00 705/3 |
| 2018/0018966 A1 | 1/2018 | Leonard |
| 2018/0121603 A1* | 5/2018 | Devarakonda ......... G16H 10/60 |
| 2019/0066849 A1* | 2/2019 | Lawrence ............. G06F 40/205 |

FOREIGN PATENT DOCUMENTS

| | | |
|---|---|---|
| CN | 105210105 A | 12/2015 |
| CN | 107368547 A | 11/2017 |

OTHER PUBLICATIONS

"Health Literacy Advisor", https://healthliteracyinnovations.com/products/hla, downloaded from the internet, May 6, 2019, 1 page.

Abrahamsson1, Emil et al., "Medical text simplification using synonym replacement: Adapting assessment of word difficulty to a compounding language", Proceedings of the 3rd Workshop on Predicting and Improving Text Readability for Target Reader Populations (PITR), Gothenburg, Sweden, Apr. 26-30, 2014, 9 pages.

Choi, Yong K.et al., "Medical Text Simplification by Medical Trainees: A Feasibility Study", ICHI 2016: 2016 IEEE International Conference on Healthcare Informatics, Oct. 4, 2016-Oct. 7, 2016, 7 pages.

Qenam, Basel et al., "Text Simplification Using Consumer Health Vocabulary to Generate Patient-Centered Radiology Reporting: Translation and Evaluation", Journal of Medical Internet Research 2017;19(12):e417, Dec. 18, 2017, 11 pages.

* cited by examiner

US 11,568,997 B2

DYNAMIC CONTEXT-BASED COLLABORATIVE MEDICAL CONCEPT INTERPRETER

BACKGROUND

The present application relates generally to an improved data processing apparatus and method and more specifically to computer mechanisms for a dynamic context-based collaborative medical concept interpreter.

Decision-support systems exist in many different industries where human experts require assistance in retrieving and analyzing information. An example is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (I-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a dynamic context-based collaborative medical concept interpreter for automatically generating and presenting summarized explanations of medical concepts. The illustrative embodiment performs natural language processing on a real-time patient-provider communication to identify one or more medical concepts referred to in the real-time patient-provider communication. The illustrative embodiment adjusts one or more previous explanations for the one or more medical concepts referred to in the real-time patient-provider communication using a set of contextual factors. The illustrative embodiment generates an abstractive summary that summarizes ranked explanations of the one or more medical concepts based on an original language used in the one or more previous explanations. The illustrative embodiment presents, in real time, the abstractive summaries of the one or more medical concepts to the patient and the provider in real-time patient-provider communication.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
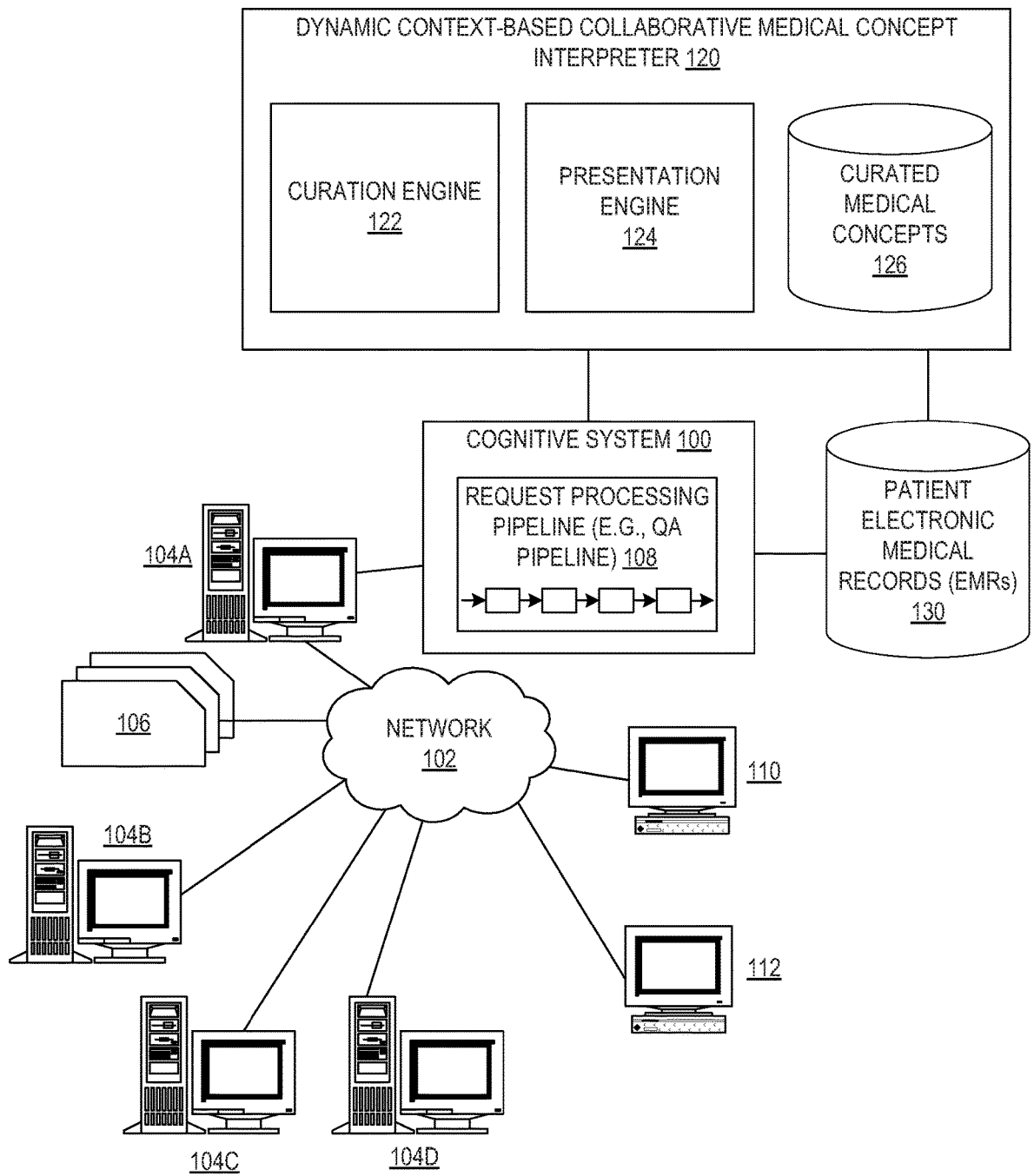
FIG. 1 depicts a schematic diagram of one illustrative embodiment of a cognitive healthcare system in a computer network.

One issue with patient-provider communications is the difficulty for patients to understand medical concepts identified by the provider. Health care providers may not always have enough time to thoroughly explain medical concepts to patients during clinical visits, in asynchronous communication settings (e.g., online secure patient-provider messaging), or the like. Additionally, a provider communicating to patients using professional terms may cause unintended consequences, such as patients' anxiety and fear about unknown medical domain knowledge for the professional language, unnecessary over-testing and overtreatment, defensive medicine, and potential distrust and conflicts between patients and their providers. Further, some patients may be unable or unwilling to ask for more information from the provider due to, for example, not wanting to look undereducated, unsure of exactly which questions to ask, or the like. Thus, using professional terms may make not effectively convey the information that health care professionals intend to communicate.

In order to address these and other issues, the illustrative embodiments provide mechanisms for a dynamic context-based collaborative medical concept interpreter. The mechanisms automatically generate and present summarized explanations of medical concepts using corpuses utilized in question and answering (Q&A) systems. By monitoring communications between a patient and a provider, the mechanism automatically identify medical concepts utilized in the communication and then extracts and summarizes explanations for those medical concepts from one or more. The mechanisms then present those summarized explanations to the patient. In one embodiment, a clinical concept may have multiple versions of explanations for patients, thus, the mechanisms may preset more than one summarized explanation for a particular medical concept.

However, based on the context of the communication between the patient and the provider, the mechanisms may select one summarized explanation over another summarized explanation based on the context of the communication. That is, different patients may prefer different explanations of the same concept because their understandings and experiences of a medical malady may be different. Some exemplary factors that may influence a patient's preferences of how medical concepts are explained may include one or more of:

Patients' prior beliefs,
Years of education and highest education levels,
Gender,
Age,
Social classes,
Stage of illness trajectory, or
Regulatory focus.

Therefore, understanding the patient's context is necessary in order to identify which version to choose for a target patient. Further, lay meanings of medical terms may change over time. Thus, automatic updating of medical concepts and their associated explanations is imperative.

Thus, a dynamic context-based collaborative medical concept interpreter of the illustrative embodiments takes into consideration the context of the communication between the patient and the provider when presenting explanations, which increases the chance of the explanations being relevant to and understandable by the patient. The dynamic context-based collaborative medical concept interpreter uses may use patient-generated questions to identify medical concepts and patient-rated answer text to construct explanations (compared to using inputs from medical experts), which allows for the identification of medical concepts that are reported by real patients as difficult to understand and explanations that are reported by real patients to be easy to understand (compared to explaining concepts that experts think are difficult to understand with explanations that experts think are easy to understand). By combining multiple explanations to construct summary texts, allows the dynamic context-based collaborative medical concept interpreter to take advantage of different explanations that are relevant to a patient's situation.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for automatically generating and presenting summarized explanations of medical concepts using corpuses utilized in question and answering (Q&A) systems. By monitoring communications between a patient and a provider, the mechanism automatically identify medical concepts utilized in the communication and then extracts and summarizes explanations for those medical concepts from one or more. The mechanisms then present those summarized explanations to the patient. In one embodiment, a clinical concept may have multiple versions of explanations for patients, thus, the mechanisms may preset more than one summarized explanation for a particular medical concept.

Figure 2:
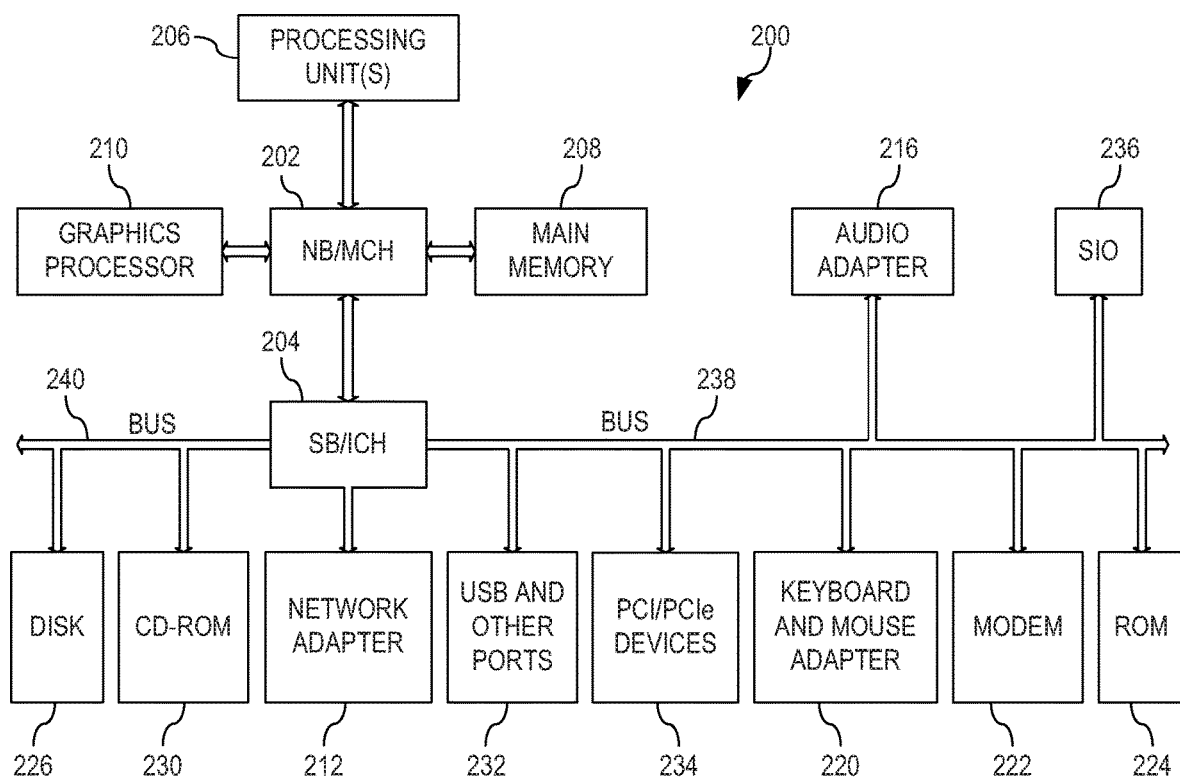
FIG. 2 is a block diagram of an example data processing system in which aspects of the illustrative embodiments are implemented.
Figure 3:
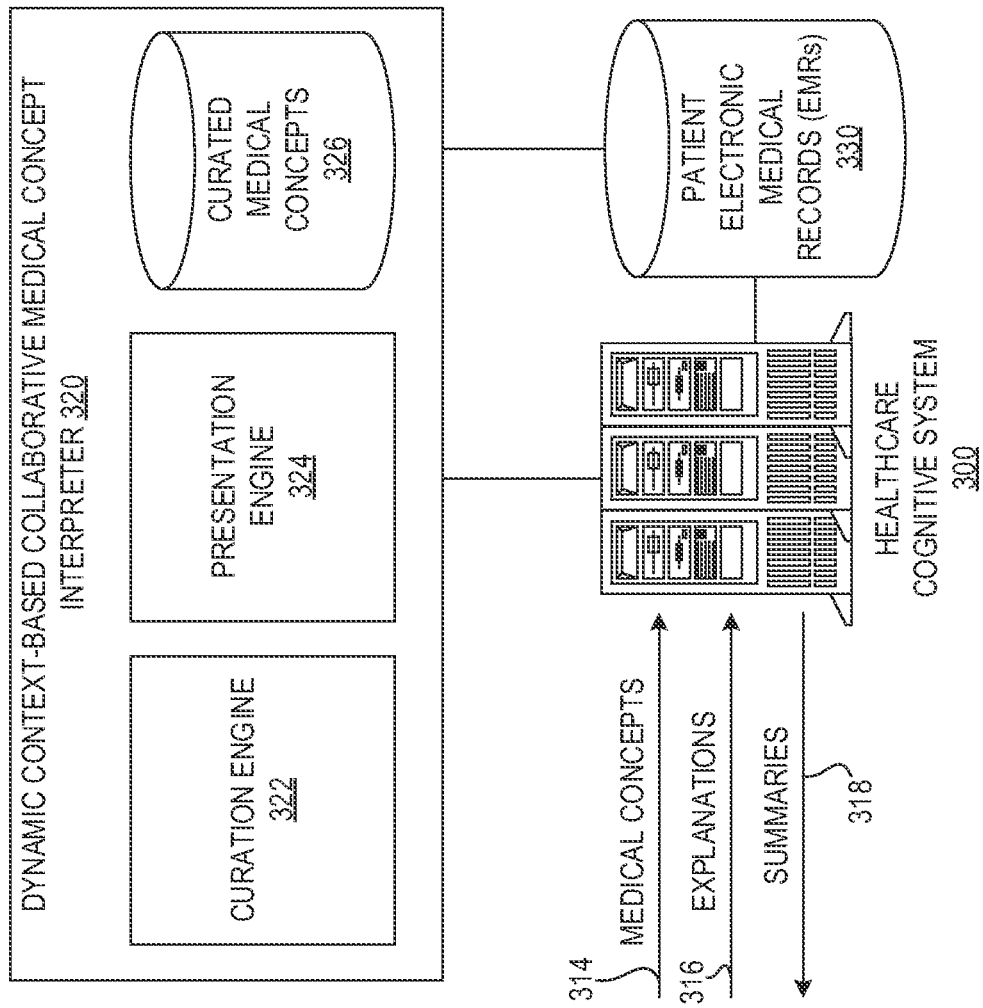
FIG. 3 is an example diagram illustrating an interaction of elements of a healthcare cognitive system in accordance with one illustrative embodiment.
Figure 3:
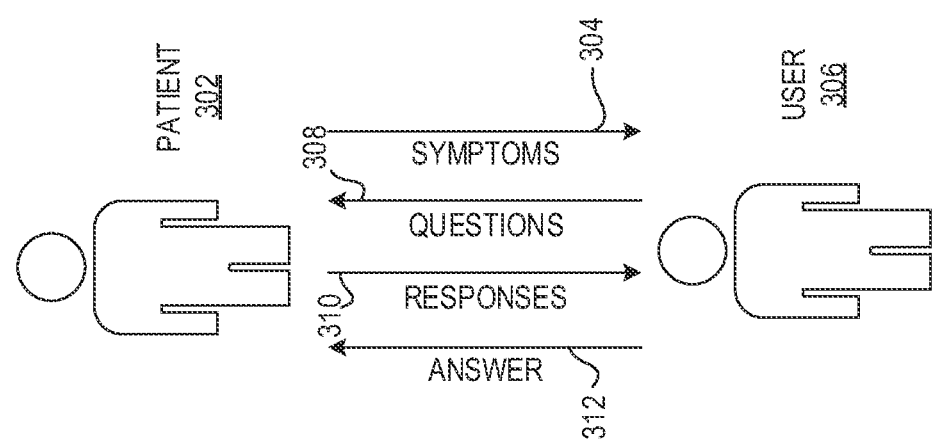

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for automatically generating and presenting summarized explanations of medical concepts using corpuses utilized in question and answering (Q&A) systems.

It should be appreciated that, the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system to include a dynamic context-based collaborative medical concept interpreter that automatically generates and presents summarized explanations of medical concepts using corpuses utilized in question and answering (Q&A) systems.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding
Ingest and process vast amounts of structured and unstructured data
Generate and evaluate hypothesis
Weigh and evaluate responses that are based only on relevant evidence
Provide situation-specific advice, insights, and guidance
Improve knowledge and learn with each iteration and interaction through machine learning processes
Enable decision making at the point of impact (contextual guidance)
Scale in proportion to the task
Extend and magnify human expertise and cognition
Identify resonating, human-like attributes and traits from natural language
Deduce various language specific or agnostic attributes from natural language
High degree of relevant recollection from data points (images, text, voice) (memorization and recall)
Predict and sense with situational awareness that mimic human cognition based on experiences
Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient electronic medical records, treatment guidance data, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that, based on a communication between a patient and a provider, analyzes a patient's EMR in relation to medical guidelines and other medical documentation in a corpus of information to automatically generate and present summarized explanations of medical concepts using corpuses utilized in question and answering (Q&A) systems.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a dynamic context-based collaborative medical concept interpreter 120 that automatically generates and presents summarized explanations of medical concepts using corpuses utilized in question and answering (Q&A) systems. Dynamic context-based collaborative medical concept interpreter 120 comprises curation engine 122 and presentation engine 124.

In order for dynamic context-based collaborative medical concept interpreter 120 to dynamically and automatically generate and present summarized explanations of medical concepts, curation engine 122 initially identifies, from patient electronic medical records (EMRs) 130, previously recorded patient-provider communication texts, such as secure messages between patients and their provider, health-related Q&A collections from online communities associated with the patients, or the like. Curation engine 122 also identifies, from patient electronic medical records (EMRs) 130, previously recorded patient-provider speech communications, such as face-to-face or phone conversations between patients and their provider during clinical visits or phone consultations, or the like. From the communication texts, speech communication, or the like, curation engine 122 performs natural language processing to identify one or more medical concepts expressed explicitly by a patient as needing explanations. That is curation engine 122 identifies questions, the focus of the questions, or the like, through question analysis using rule-based sentence features identified using natural language processing.

Using the identified one or more medical concepts, curation engine 122 identifies provider explanations of the one or more medical concepts in patient electronic medical records (EMRs) 130 from the contextual text or speech surrounding the moments when the one or more medical concepts are mentioned. Curation engine 122 stores each medical concept with connections to their corresponding explanations in a curated medical concept data structure 126. From the text surrounding the one or more medical concepts and the associated explanations, curation engine 122 identifies corresponding context, such as community context (e.g., address, city, zip code, or the like), family context (e.g., parents, siblings, children, family health history, or the like), individual context (e.g., race, gender, education, or the like), health conditions, treatments, response to treatments, physician types, health training programs attended/education received, emotions, lexical complexity, or the like. Curation engine 122 may identify the context for the one or more medical concepts and the associated explanations using rule-based keyword extraction, sentiment and lexical complexity analysis, or the like. Curation engine 122 stores each identified context for each of the one or more medical concepts and identified context for each explanation associated with the one or more medical concepts in curated medical concept data structure 126.

Utilizing the identified contexts associated with the explanations of the one or more medical concepts, curation engine 122 produces a ranked list of the explanations in curated medical concept data structure 126 as providing an answer to the medical concept based on the context surrounding the associated medical concept, i.e. whether the explanation provide an answer to the medical concept under question based on the context that surrounded the question from which the medical concept was identified. Curation engine 122 may perform the ranking either explicitly or implicitly based on a, for example: a rating the explanations (e.g., best answer, numerical rating, or the like) as in Q&A web sites with consumer-generated text [explicit] or expressing an understanding of the explanation (e.g., "Now I understand when you put it that way" for a good answer, "I still don't understand" for a bad answer) [implicit]. Curation engine 122 stores the ranked list in curated medical concept data structure 126. Therefore, curation engine 122 generates a context-based explanation ranking model for explanations of medical concepts that is learned using the contextual features of the concepts and the explanations to rank the explanations.

Then, in a real-time patient-provider communication setting, such as an in-progress patient-provider secure messaging, face-to-face clinical visit, or other synchronous or asynchronous patient-provider communication, presentation engine 124 utilizes natural language processing to identify one or more medical concepts that are referred to in the real-time patient-provider communication setting. Using the context-based explanation ranking model generated by curation engine 122, i.e. the one or more medical concepts (questions), provider explanations (answers), identified contexts for the one or more medical concepts, the contexts for explanations associated with the one or more medical concepts, and the ranked list of explanations for medical concepts with given contexts and the identified one or more medical concepts that are referred to in the real-time patient-provider communication setting, presentation engine 124 adjusts explanations of the one or more medical concepts that are referred to in the real-time patient-provider communication setting by ranking the explanations based on contextual factors surrounding the patient, such as previous patient-provider communication, patient's health conditions, patient's interactions with dynamic context-based collaborative medical concept interpreter 120, or the like.

Presentation engine 124 then generates an abstractive summary that summarizes top explanations of the one or more medical concepts based on the original language used in those explanations. Presentation engine 124 determines a number of explanations used as the top explanations by sampling the next n explanations on the ranked list. If the keywords in those explanations do not differ from those in the highlighted content, then the number of explanations used as the top explanations is all explanations examined before the sampling window. Presentation engine 124 then presents the abstractive summaries of those medical concepts to patients and their providers in patient-provider communication settings in real time, such as though a display where the summaries of medical concepts appear in a pop-up, a display where patients mouse-over medical concepts in their providers' secure messages, a side panel on patient-provider shared display, or the like, during an in-progress patient-provider secure messaging, face-to-face clinical visit, or other synchronous or asynchronous patient-provider communication.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to automatically generate and present summarized explanations of medical concepts to patients and/or using corpuses utilized in question and answering (Q&A) systems. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, provider, technician, or the like. The user 306 may interact with the patient 302 via a question 308 and response 310 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In the question 308 and response 310 exchange, some responses 310 may be in the form of questions from patient 302 about medical concepts that user 306 indicated in questions 308. Based on such questions in responses 310, user 306 may provide an answer 312 in the form of an explanation of the medical concepts, in accordance with the illustrative embodiments herein, the healthcare cognitive system 300 is augmented to include logic implemented in specialized hardware, software executed on hardware, or any combination of specialized hardware and software executed on hardware, for implementing a dynamic context-based collaborative medical concept interpreter 320 that automatically generates and presents summarized explanations of medical concepts using corpuses utilized in question and answering (Q&A) systems. Dynamic context-based collaborative medical concept interpreter 320 comprises curation engine 322 and presentation engine 324.

In order for dynamic context-based collaborative medical concept interpreter 320 to dynamically and automatically generate and present summarized explanations of medical concepts, curation engine 322 initially identifies, from patient electronic medical records (EMRs) 330, previously recorded patient-provider communication texts, such as secure messages between patients and their providers, health-related Q&A collections from online communities associated with the patients, or the like. Curation engine 322 also identifies, from patient electronic medical records (EMRs) 330, previously recorded patient-provider speech communications, such as face-to-face or phone conversations between patients and their provider during clinical visits or phone consultations, or the like. From the communication texts, speech communication, or the like, curation engine 322 performs natural language processing to identify one or more medical concepts expressed explicitly by a patient as needing explanations. That is curation engine 322 identifies questions, the focus of the questions, or the like, through question analysis using rule-based sentence features identified using natural language processing.

Using the identified one or more medical concepts, curation engine 322 identifies provider explanations of the one or more medical concepts in patient electronic medical records (EMRs) 330 from the contextual text or speech surrounding the moments when the one or more medical concepts are mentioned. Curation engine 322 stores each medical concept with connections to their corresponding explanations in a curated medical concept data structure 326. From the text surrounding the one or more medical concepts and the associated explanations, curation engine 322 identifies corresponding context, such as community context (e.g., address, city, zip code, or the like), family context (e.g., parents, siblings, children, family health history, or the like), individual context (e.g., race, gender, education, or the like), health conditions, treatments, response to treatments, physician types, health training programs attended/education received, emotions, lexical complexity, or the like. Curation engine 322 may identify the context for the one or more medical concepts and the associated explanations using rule-based keyword extraction, sentiment and lexical complexity analysis, or the like. Curation engine 322 stores each identified context for each of the one or more medical concepts and identified context for each explanation associated with the one or more medical concepts in curated medical concept data structure 326.

Utilizing the identified contexts associated with the explanations of the one or more medical concepts, curation engine 322 produces a ranked list of the explanations in curated medical concept data structure 326 as providing an answer to the medical concept based on the context surrounding the associated medical concept, i.e. whether the explanation provide an answer to the medical concept under question based on the context that surrounded the question from which the medical concept was identified. Curation engine 322 may perform the ranking either explicitly or implicitly based on a, for example: a rating the explanations (e.g., best answer, numerical rating, or the like) as in Q&A web sites with consumer-generated text [explicit] or expressing an understanding of the explanation (e.g., "Now I understand when you put it that way" for a good answer, "I still don't understand" for a bad answer) [implicit]. Curation engine 322 stores the ranked list in curated medical concept data structure 326. Therefore, curation engine 322 generates a context-based explanation ranking model for explanations of medical concepts that is learned using the contextual features of the concepts and the explanations to rank the explanations.

Then, in a real-time patient 302/user 306 communication setting, such as an in-progress patient 302/user 306 secure messaging, face-to-face clinical visit, or other synchronous or asynchronous patient 302/user 306 communication, presentation engine 324 utilizes natural language processing to identify one or more medical concepts 314 that are referred to in the real-time patient 302/user 306 communication setting. Using the context-based explanation ranking model generated by curation engine 322, i.e. the one or more medical concepts (questions), provider explanations (answers), identified contexts for the one or more medical concepts, the contexts for explanations associated with the one or more medical concepts, and the ranked list of explanations for medical concepts with given contexts in curated medical concepts data structure 326 and the identified one or more medical concepts 314 that are referred to in the real-time patient 302/user 306 communication setting, presentation engine 324 adjusts explanations 316 of the one or more medical concepts 314 that are referred to in the real-time patient 302/user 306 communication setting by ranking explanations 316 based on contextual factors surrounding patient 302, such as previous patient 302/user 306 communication, patient's 302 health conditions, patient's 302 interactions with dynamic context-based collaborative medical concept interpreter 320, or the like.

Presentation engine 324 then generates an abstractive summary that summarizes top explanations of the one or more medical concepts based on the original language used in those explanations. Presentation engine 124 determines a number of explanations used as the top explanations by sampling the next n explanations on the ranked list. If the keywords in those explanations do not differ from those in the highlighted content, then the number of explanations used as the top explanations is all explanations examined before the sampling window. Presentation engine 324 then presents abstractive summaries 318 of those medical concepts 314 to patient 302 and user 306 in patient 302/user 306 communication settings in real time, such as though a display where abstractive summaries 318 of medical concepts appear in a pop-up, a display where patient 302 mouses-over medical concepts in their user's 306 secure messages, a side panel on patient 302/user 306 shared display, or the like, during an in-progress patient 302/user 306 secure messaging, face-to-face clinical visit, or other synchronous or asynchronous patient 302/user 306 communication.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that, the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
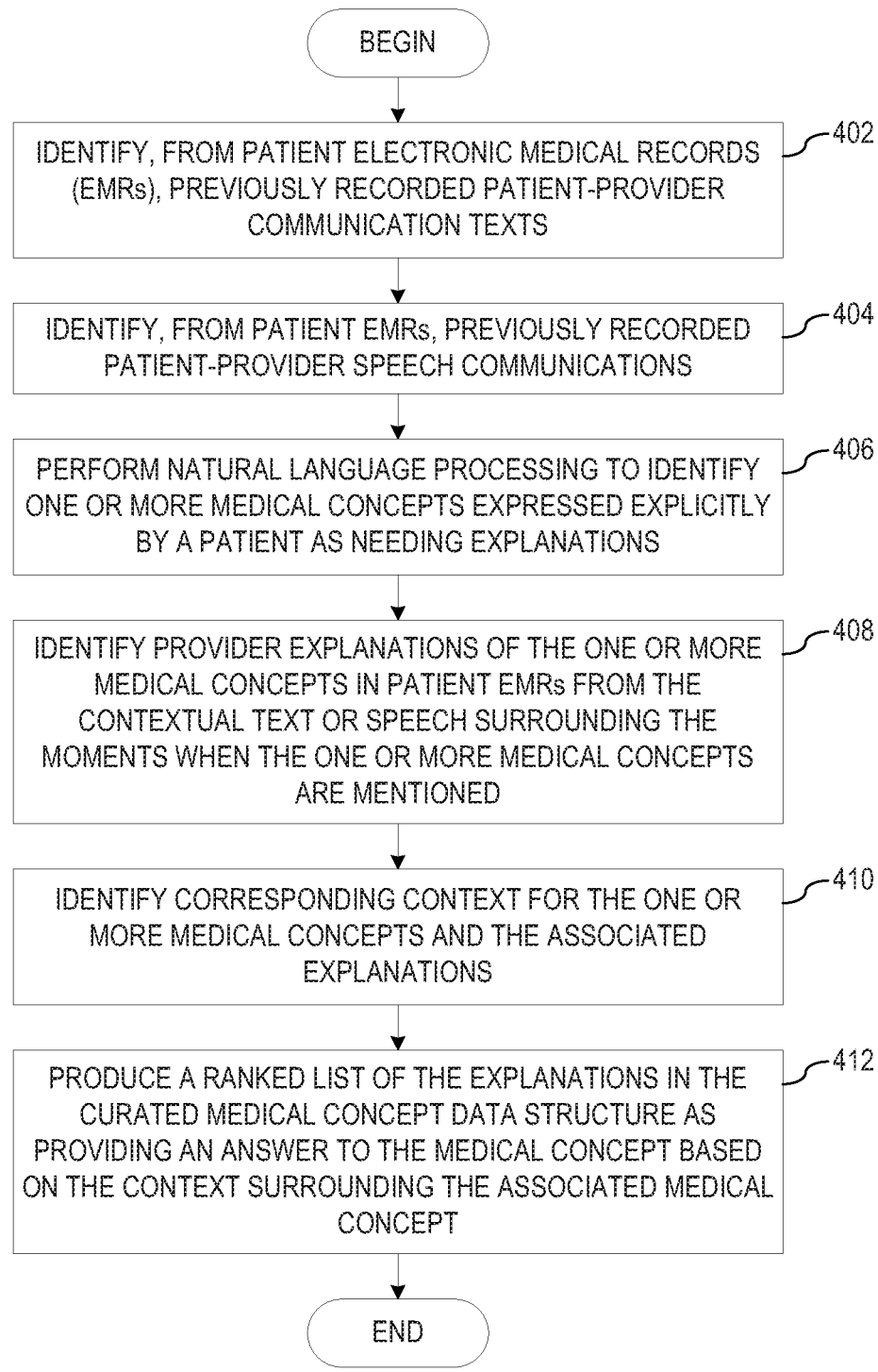
FIG. 4 depicts an exemplary flowchart of the operations performed in curating medical concepts and explanations form communications between a patient and a provider in accordance with an illustrative embodiment.

FIG. 4 depicts an exemplary flowchart of the operations performed in curating medical concepts and explanations form communications between a patient and a provider in accordance with an illustrative embodiment. As the operation begins, the dynamic context-based collaborative medical concept interpreter identifies, from patient electronic medical records (EMRs), previously recorded patient-provider communication texts (step 402), such as secure messages between patients and their providers, health-related Q&A collections from online communities associated with the patients, or the like. The dynamic context-based collaborative medical concept interpreter further identifies, from patient electronic medical records (EMRs), previously recorded patient-provider speech communications (step 404), such as face-to-face or phone conversations between patients and their provider during clinical visits or phone consultations, or the like. From the communication texts, speech communication, or the like, the dynamic context-based collaborative medical concept interpreter performs natural language processing to identify one or more medical concepts expressed explicitly by a patient as needing explanations (step 406). That is, dynamic context-based collaborative medical concept interpreter identifies questions, the focus of the questions, or the like, through question analysis using rule-based sentence features identified using natural language processing.

Using the identified one or more medical concepts, the dynamic context-based collaborative medical concept interpreter identities provider explanations of the one or more medical concepts in patient electronic medical records (EMRs) from the contextual text or speech surrounding the moments when the one or more medical concepts are mentioned (step 408). The dynamic context-based collaborative medical concept interpreter stores each medical concept with connections to their corresponding explanations in a curated medical concept data structure. From the text surrounding the one or more medical concepts and the associated explanations, the dynamic context-based collaborative medical concept interpreter identifies corresponding context (step 410), such as community context (e.g., address, city, zip code, or the like), family context (e.g., parents, siblings, children, family health history, or the like), individual context (e.g., race, gender, education, or the like), health conditions, treatments, response to treatments, physician types, health training programs attended/education received, emotions, lexical complexity, or the like. The dynamic context-based collaborative medical concept interpreter may identify the context for the one or more medical concepts and the associated explanations using rule-based keyword extraction, sentiment and lexical complexity analysis, or the like. The dynamic context-based collaborative medical concept interpreter stores each identified context for each of the one or more medical concepts and identified context for each explanation associated with the one or more medical concepts in the curated medical concept data structure.

Utilizing the identified contexts associated with the explanations of the one or more medical concepts, dynamic context-based collaborative medical concept interpreter produces a ranked list of the explanations in the curated medical concept data structure as providing an answer to the medical concept based on the context surrounding the associated medical concept (step 412), i.e. whether the explanation provide an answer to the medical concept under question based on the context that surrounded the question from which the medical concept was identified. The dynamic context-based collaborative medical concept interpreter may perform the ranking either explicitly or implicitly based on a, for example: a rating the explanations (e.g., best answer, numerical rating, or the like) as in Q&A web sites with consumer-generated text [explicit] or expressing an understanding of the explanation (e.g., "Now I understand when you put it that way" for a good answer, "I still don't understand" for a bad answer) [implicit]. The dynamic context-based collaborative medical concept interpreter stores the ranked list in the curated medical concept data structure. Therefore, the dynamic context-based collaborative medical concept interpreter generates a context-based explanation ranking model for explanations of medical concepts that is learned using the contextual features of the concepts and the explanations to rank the explanations, with the operation ending thereafter.

Figure 5:
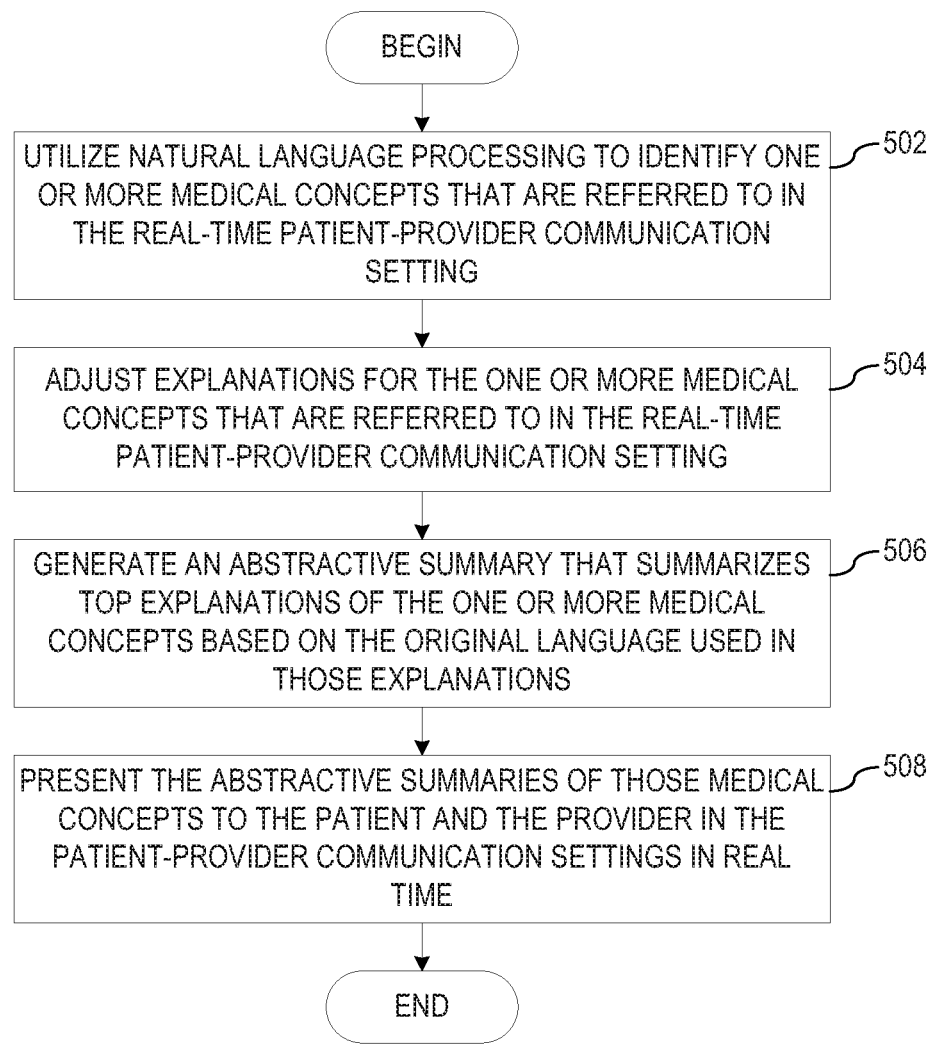
FIG. 5 depicts an exemplary flowchart of the operations performed in automatically generate and present summarized explanations of medical concepts in accordance with an illustrative embodiment.

FIG. 5 depicts an exemplary flowchart of the operations performed in automatically generate and present summarized explanations of medical concepts in accordance with an illustrative embodiment. As the operation begins, in a real-time patient-provider communication setting, such as an in-progress patient-provider secure messaging, face-to-face clinical visit, or other synchronous or asynchronous patient-provider communication, the dynamic context-based collaborative medical concept interpreter utilizes natural language processing to identify one or more medical concepts that are referred to in the real-time patient-provider communication setting (step 502). Using a previously generated context-based explanation ranking model, i.e. the one or more medical concepts (questions), provider explanations (answers), identified contexts for the one or more medical concepts, the contexts for explanations associated with the one or more medical concepts, and the ranked list of explanations for medical concepts with given contexts in a curated medical concepts data structure and the identified one or more medical concepts that are referred to in the real-time patient-provider communication setting, the dynamic context-based collaborative medical concept interpreter adjusts explanations for the one or more medical concepts that are referred to in the real-time patient-provider communication setting (step 504) by ranking the explanations based on contextual factors surrounding the patient, such as previous patient-provider communication, patient's health conditions, patient's interactions with the dynamic context-based collaborative medical concept interpreter, or the like.

The dynamic context-based collaborative medical concept interpreter then generates an abstractive summary that summarizes top explanations of the one or more medical concepts based on the original language used in those explanations (step 506). The dynamic context-based collaborative medical concept interpreter determines a number of explanations used as the top explanations by sampling the next n explanations on the ranked list. If the keywords in those explanations do not differ from those in the highlighted content, then the number of explanations used as the top explanations is all explanations examined before the sampling window. The dynamic context-based collaborative medical concept interpreter then presents the abstractive summaries of those medical concepts to the patient and the provider in the patient-provider communication settings in real time (step 508). The presentation may be through a display where abstractive summaries of medical concepts appear in a pop-up, a display where the patient mouses-over medical concepts in their provider's secure messages, a side panel on a patient-provider shared display, or the like, during an in-progress patient-provider secure messaging, face-to-face clinical visit, or other synchronous or asynchronous patient-provider communication. The operation ends thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for a dynamic context-based collaborative medical concept interpreter. The mechanisms automatically generate and present summarized explanations of medical concepts using corpuses utilized in question and answering (Q&A) systems. By monitoring communications between a patient and a provider, the mechanism automatically identify medical concepts utilized in the communication and then extracts and summarizes explanations for those medical concepts from one or more. The mechanisms then present those summarized explanations to the patient. In one embodiment, a clinical concept may have multiple versions of explanations for patients, thus, the mechanisms may preset more than one summarized explanation for a particular medical concept.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to specifically configure the at least one processor to be a dynamic context-based collaborative medical concept interpreter for automatically generating and presenting summarized explanations of medical concepts, the method comprising the dynamic context-based collaborative medical concept interpreter:

executing computer executed natural language processing on recorded patient-provider communications to identify one or more portions of content in the recorded patient-provider communications referencing one or more previous medical concepts expressed in the one or more portions of content in a format that explicitly indicates that the previous medical concept is needing explanation, wherein the previously recorded patient-provider communications are stored data structures comprising recorded textual data or recorded audio data;

executing computer executed natural language processing on contextual content, surrounding the one or more previous medical concepts, in the recorded textual data or recorded audio data, to identify provider explanations of the one or more previous medical concepts in patient electronic medical records (EMRs), thereby forming one or more previous explanations;

executing at least one of computer executed rule-based keyword extraction or computer executed sentiment and lexical complexity analysis on the contextual content to identify patient context data for a patient providing the contextual content;

generating a curated medical concept data structure that connects each of the one or more medical concepts to corresponding provider explanations and corresponding patient context data;

generating a context-based explanation ranking computer model based on the curated medical concept data structure, wherein the context-based explanation ranking computer model, for a given medical concept and context, ranks corresponding previous explanations in the one or more previous explanations;

executing computer executed natural language processing on a real-time patient-provider communication between a current patient and a provider, to identify one or more current medical concepts referred to in the real-time patient-provider communication;

processing the real-time patient-provider communication by applying the context-based explanation ranking computer model to the real-time patient-provider communication based on the one or more current medical concepts, which re-ranks one or more previous explanations for the one or more current medical concepts referred to in the real-time patient-provider communication using a set of contextual factors associated with the current patient;

generating an abstractive summary that summarizes the re-ranked one or more previous explanations of the one or more current medical concepts based on an original language used in the one or more previous explanations; and presenting, the abstractive summary of the one or more current medical concepts to the current patient in real-time as part of a display corresponding to the real-time patient-provider communication, wherein executing computer executed natural language processing on recorded patient-provider communications comprises executing a computer executed rule-based sentence feature identification operation that identifies the one or more portions of content having the format at least by identifying the one or more portions of content as comprising one or more questions and one or more foci of the one or more questions.

2. The method of claim 1, wherein the contextual factors associated with the current patient are one or more of previous patient-provider communications, the current patient's health conditions, or the current patient's interactions with the dynamic context-based collaborative medical concept interpreter.

3. The method of claim 1, wherein processing the real-time patient-provider communication by applying the context-based explanation ranking computer model to the real-time patient-provider communication comprises re-ranking the one or more previous explanations based on the one or more previously identified medical concepts, one or more previously identified provider explanations, contexts for the one or more previously identified medical concepts, contexts for the one or more previously identified provider explanations associated with the one or more previously identified medical concepts, and a ranked list of explanations for the one or more previously identified medical concepts with given contexts.

4. The method of claim 1, wherein generating the context-based explanation ranking computer model comprises:

identifying a ranking context associated with each of the one or more previous medical concepts and the one or more previous explanations; and generate, for each previous medical concept in the one or more previous medical concepts, a ranked listing of corresponding previous explanations as providing an a patient understandable explanation of the previous medical concept based on the ranking context associated with the previous medical concept.

5. The method of claim 4, wherein the ranking context comprises one of an explicit ranking specifying a numerical rating of one or more previous explanations by one or more users, or an implicit ranking based on keywords present in the one or more portions of content that indicate a level of understanding by the one or more users.

6. The method of claim 1, wherein the contextual content comprises one or more of community context, family context, individual context, health conditions, treatments, response to treatments, physician types, health training programs attended/education received, emotions, or lexical complexity.

7. The method of claim 4, wherein the ranking context is identified by executing computer executed rule-based keyword extraction or computer executed sentiment and lexical complexity analysis on the one or more portions of content of the recorded patient-provider communications.

8. A computer program product comprising a computer readable storage medium having a computer readable program stored therein, wherein the computer readable program, when executed on a computing device, causes the computing device to implement a dynamic context-based collaborative medical concept interpreter for automatically generating and presenting summarized explanations of medical concepts which operates to:

execute computer executed natural language processing on recorded patient-provider communications to identify one or more portions of content in the recorded patient-provider communications referencing one or more previous medical concepts expressed in the one or more portions of content in a format that explicitly indicates that the previous medical concept is needing explanation, wherein the previously recorded patient-provider communications are stored data structures comprising recorded textual data or recorded audio data;

execute computer executed natural language processing on contextual content, surrounding the one or more previous medical concepts, in the recorded textual data or recorded audio data, to identify provider explanations of the one or more previous medical concepts in patient electronic medical records (EMRs), thereby forming one or more previous explanations;

execute at least one of computer executed rule-based keyword extraction or computer executed sentiment and lexical complexity analysis on the contextual content to identify patient context data for a patient providing the contextual content;

generate a curated medical concept data structure that connects each of the one or more medical concepts to corresponding provider explanations and corresponding patient context data;

generate a context-based explanation ranking computer model based on the curated medical concept data structure, wherein the context-based explanation ranking computer model, for a given medical concept and context, ranks corresponding previous explanations in the one or more previous explanations;

execute computer executed natural language processing on a real-time patient-provider communication between a current patient and a provider, to identify one or more current medical concepts referred to in the real-time patient-provider communication;

executing computer executed natural language processing on a real-time patient-provider communication between a current patient and a provider, to identify one or more current medical concepts referred to in the real-time patient-provider communication;

process the real-time patient-provider communication by applying the context-based explanation ranking computer model to the real-time patient-provider communication based on the one or more current medical concepts, which re-ranks one or more previous explanations for the one or more current medical concepts referred to in the real-time patient-provider communication using a set of contextual factors associated with the current patient;

generate an abstractive summary that summarizes the re-ranked one or more previous explanations of the one or more current medical concepts based on an original language used in the one or more previous explanations; and present the abstractive summary of the one or more current medical concepts to the current patient in real-time as part of a display corresponding to the real-time patient-provider communication, wherein executing computer executed natural language processing on recorded patient-provider communications comprises executing a computer executed rule-based sentence feature identification operation that identifies the one or more portions of content having the format at least by identifying the one or more portions of content as comprising one or more questions and one or more foci of the one or more questions.

9. The computer program product of claim 8, wherein the contextual factors associated with the current patient are one or more of previous patient-provider communications, the current patient's health conditions, or the current patient's interactions with the dynamic context-based collaborative medical concept interpreter.

10. The computer program product of claim 8, wherein the computer readable program to process the real-time patient-provider communication by applying the context-based explanation ranking computer model to the real-time patient-provider communication at least by re-ranking the one or more previous explanations based on the one or more previously identified medical concepts, one or more previously identified provider explanations, contexts for the one or more previously identified medical concepts, contexts for the one or more previously identified provider explanations associated with the one or more previously identified medical concepts, and a ranked list of explanations for the one or more previously identified medical concepts with given contexts.

11. The computer program product of claim 8, wherein the computer readable program generates the context-based explanation ranking computer model at least by causing the computing device to:
   identify a ranking context associated with each of the one or more previous medical concepts and the one or more previous explanations; and
   generate, for each previous medical concept in the one or more previous medical concepts, a ranked listing of corresponding previous explanations as providing an a patient understandable explanation of the previous medical concept based on the ranking context associated with the previous medical concept.

12. The computer program product of claim 11, wherein the ranking context comprises one of an explicit ranking specifying a numerical rating of one or more previous explanations by one or more users, or an implicit ranking based on keywords present in the one or more portions of content that indicate a level of understanding by the one or more users.

13. The computer program product of claim 8, wherein the contextual content comprises one or more of community context, family context, individual context, health conditions, treatments, response to treatments, physician types, health training programs attended/education received, emotions, or lexical complexity.

14. The computer program product of claim 11, wherein the ranking context is identified by executing computer executed rule-based keyword extraction or computer executed sentiment and lexical complexity analysis on the one or more portions of content of the recorded patient-provider communications.

15. An apparatus comprising:
   at least one processor; and
   at least one memory coupled to the at least one processor, wherein the at least one memory comprises instructions which, when executed by the at least one processor, cause the at least one processor to implement a dynamic context-based collaborative medical concept interpreter for automatically generating and presenting summarized explanations of medical concepts, which operates to:

execute computer executed natural language processing on recorded patient-provider communications to identify one or more portions of content in the recorded patient-provider communications referencing one or more previous medical concepts expressed in the one or more portions of content in a format that explicitly indicates that the previous medical concept is needing explanation, wherein the previously recorded patient-provider communications are stored data structures comprising recorded textual data or recorded audio data;

execute computer executed natural language processing on contextual content, surrounding the one or more previous medical concepts, in the recorded textual data or recorded audio data, to identify provider explanations of the one or more previous medical concepts in patient electronic medical records (EMRs), thereby forming one or more previous explanations;

execute at least one of computer executed rule-based keyword extraction or computer executed sentiment and lexical complexity analysis on the contextual content to identify patient context data for a patient providing the contextual content;

generate, by the curation engine, a curated medical concept data structure that connects each of the one or more medical concepts to corresponding provider explanations and corresponding patient context data;

generate, by the curation engine, a context-based explanation ranking computer model based on the curated medical concept data structure, wherein the context-based explanation ranking computer model, for a given medical concept and context, ranks corresponding previous explanations in the one or more previous explanations;

execute computer executed natural language processing on a real-time patient-provider communication between a current patient and a provider, to identify one or more current medical concepts referred to in the real-time patient-provider communication;

process the real-time patient-provider communication by applying the context-based explanation ranking computer model to the real-time patient-provider communication based on the one or more current medical concepts, which re-ranks one or more previous explanations for the one or more current medical concepts referred to in the real-time patient-provider communication using a set of contextual factors associated with the current patient;

generate an abstractive summary that summarizes the re-ranked one or more previous explanations of the one or more current medical concepts based on an original language used in the one or more previous explanations; and present the abstractive summary of the one or more current medical concepts to the current patient in real-time as part of a display corresponding to the real-time patient-provider communication, wherein executing computer executed natural language processing on recorded patient-provider communications comprises executing a computer executed rule-based sentence feature identification operation that identifies the one or more portions of content having the format at least by identifying the one or more portions of content as comprising one or more questions and one or more foci of the one or more questions.

16. The apparatus of claim 15, wherein the instructions cause the curation engine to generate the context-based explanation ranking computer model at least by causing the curation engine executing on the at least one processor to:
  identify a ranking context associated with each of the one or more previous medical concepts and the one or more previous explanations; and
  generate, for each previous medical concept in the one or more previous medical concepts, a ranked listing of corresponding previous explanations as providing an a patient understandable explanation of the previous medical concept based on the ranking context associated with the previous medical concept.

17. The method of claim 1, wherein the one or more medical concepts are one or more medical concepts specified in the one or more foci of the one or more questions.

18. The method of claim 1, wherein executing computer executed natural language processing on real-time patient provider communication between a current patient and a provider comprises processing the real-time patient provider communication through a question answering system comprising one or more question processing pipelines of computer executed reasoning algorithms, to generate one or more candidate answers to a natural language question present in the real-time patient provider communication.

19. The method of claim 18, wherein the one or more current medical concepts referred to in the real-time patient-provider communication are one or more current medical concepts referred to in the natural language question present in the real-time patient provider communication.

\* \* \* \* \*